(12) United States Patent
Mason

(10) Patent No.: US 11,540,939 B2
(45) Date of Patent: Jan. 3, 2023

(54) COOLING PACK

(71) Applicant: 2256385 Ontario Inc., Mono (CA)

(72) Inventor: Andrew John Mason, Mono (CA)

(73) Assignee: 2256385 Ontario Inc.

( * ) Notice: Subject to any disclaimer, the term of this patent is extended or adjusted under 35 U.S.C. 154(b) by 725 days.

(21) Appl. No.: 16/178,675

(22) Filed: Nov. 2, 2018

(65) Prior Publication Data

US 2019/0133819 A1    May 9, 2019

Related U.S. Application Data

(60) Provisional application No. 62/582,656, filed on Nov. 7, 2017.

(51) Int. Cl.
```
A61F 7/10      (2006.01)
A61F 7/00      (2006.01)
A61F 7/02      (2006.01)
```

(52) U.S. Cl.
CPC ............ *A61F 7/103* (2013.01); *A61F 7/10* (2013.01); *A61F 7/106* (2013.01); *A61F 2007/0048* (2013.01); *A61F 2007/022* (2013.01); *A61F 2007/0249* (2013.01); *A61F 2007/105* (2013.01); *A61F 2007/108* (2013.01)

(58) Field of Classification Search
CPC .............................................. A61F 2007/0048
See application file for complete search history.

(56) References Cited

U.S. PATENT DOCUMENTS

| | | | |
|---|---|---|---|
| 3,736,769 A | | 6/1973 | Petersen |
| 4,240,436 A | * | 12/1980 | Singleton .................. A61F 7/10 606/191 |
| 4,253,464 A | | 3/1981 | Zorgniotti et al. |
| 4,404,820 A | | 9/1983 | Romaine |
| 5,243,974 A | | 9/1993 | Allen |
| 6,068,607 A | | 5/2000 | Palmer et al. |
| 8,128,675 B2 | | 3/2012 | Nahhas |
| 2005/0193742 A1 | | 9/2005 | Arnold |
| 2008/0010716 A1 | | 1/2008 | Brown et al. |
| 2010/0094386 A1 | | 4/2010 | Margolis et al. |
| 2012/0089212 A1 | * | 4/2012 | Benda ........................ A61F 7/02 607/108 |
| 2012/0316626 A1 | | 12/2012 | Dolivier et al. |
| 2013/0158635 A1 | * | 6/2013 | Federico ................... A61F 7/10 607/108 |
| 2015/0025305 A1 | | 1/2015 | Stringer et al. |
| 2016/0346116 A1 | * | 12/2016 | Ohmer ...................... A61F 7/08 |

FOREIGN PATENT DOCUMENTS

| CN | 2681717 | 3/2005 |
|---|---|---|
| CN | 203353697 U | 12/2013 |

\* cited by examiner

*Primary Examiner* — Kaitlyn E Smith
(74) *Attorney, Agent, or Firm* — Price Heneveld LLP

(57) ABSTRACT

Described are various embodiments of a cooling pack. In one such embodiment a cooling pack is provided for cooling a crotch region of a human while seated on a seating surface, the cooling pack comprising a tapered container for holding a cooling material therein, and defined by tapering upper and lower surfaces drawing into a tapered edge to be positioned between the crotch region and the seating surface in use, thereby providing cooling for the region.

13 Claims, 6 Drawing Sheets

COOLING PACK

CROSS-REFERENCE TO RELATED APPLICATION

This application claims the benefit of U.S. Patent Application No. 62/582,656, filed Nov. 7, 2017, which is incorporated herein by reference in its entirety.

FIELD OF THE DISCLOSURE

The present disclosure relates to cooling packs, and, in particular, to a cooling pack for cooling the crotch region of a human.

BACKGROUND

Various cooling packs are known in the art and generally consist of a container or receptacle to be filed with, or enclosing, a cooling material such as water/ice or gel. Such cooling packs may be generically applied for different uses.

Numerous therapeutic benefits arise from cooling of the scrotum and testes region. It is well known that a relationship exists between elevated testes temperature and decreased sperm quality and quantity. Elevated testes temperature is caused by or correlated with several circumstances such as remaining in a sitting posture for an extended period of time, driving a vehicle, obesity, presence of varicocele, and wearing of clothing. Cooling of the testes and scrotum can counteract this propensity for elevated testes temperature.

Cooling of the scrotum and testes is often recommended to reduce pain, inflammation, and swelling after surgery in this region, such as after vasectomy, varicocelectomy, surgery to correct testicular torsion, and other surgeries involving incisions of the scrotum and the anatomy contained therein. Moreover, cooling of the scrotum and testes may also offer comfort and means of therapeutic relaxation to the user on hot days to reduce feelings of discomfort and sweating. Finally, cooling of the testes may optimize the body's ability to produce testosterone.

Several existing solutions for cooling the scrotum and testes involve garments that position ice or cooling liquid against the scrotum or testes. However, these are complex, costly, may be socially awkward if bulging from pants in professional settings such as an office place, may be cumbersome or prohibitive during walking or other movement, and may require access to a private room for the user to replenish the ice packs. They also require the user to deviate from their normal preferred clothing which may be uncomfortable or undesirable.

One existing solution for cooling the scrotum and testes involves wrapping a towel around and sitting on a bag of frozen peas. However, the shape of the bag of peas is generally too large and not the right shape to target the scrotum and testes, causing unwanted cooling of the user's legs and perineum which may cause discomfort. Furthermore, the bag of peas will be of inconsistent shape both upon initial application and as it thaws, possibly causing initial discomfort from pressure points if initially frozen solid into a rough shape, and later possibly causing inconsistent contact leading to inconsistent cooling as it thaws and its shape collapses. This effect can be exacerbated if the bag of peas has previously been thawed then re-frozen. The towel thermal conductivity can also be inconsistent depending on how many layers are wrapped, or if the towel absorbs water over time due to condensation. Moreover, the bag of peas often has a thin wall of plastic that is easily punctured and may leak and stain clothing or upholstery. In addition, the towel allows air to penetrate causing condensation which may lead to the towel becoming wet, possibly leading to unwanted wetting of the user's pants. Finally, the user generally must position the bag of peas and towel before sitting on them, and must rise to reposition them. This is not as convenient as a cooling device that can be comfortably applied, removed, or repositioned without leaving the sitting position.

Another existing solution for cooling the scrotum and testes involves wrapping a towel around and sitting on a hard-sided ice pack with general shape of a rectangular prism, as is commonly used for keeping lunches cool. This rectangular prism shape is not compatible with the shape of the legs, scrotum, testes, and perineum when in the sitting position, causing discomfort from contact with legs and possible perineum, and possible discomfort from too much upwards pressure on the scrotum and testes or insufficient contact between the ice pack and the scrotum and testes if the gap between scrotum and testes and chair surface is higher than the ice pack thickness. Furthermore, the aforementioned drawbacks of using a towel persist.

A similar method for cooling the scrotum and testes involves a fabric-enveloped soft-sided pouch that is to be sat on, containing both cold liquid held above its freezing point and cold solid spheres that may or may not be frozen solid. However, because it is too compliant, this solution doesn't provide effective contact with the testes, and because it is a generally flat shape, it provides little adjustability for different distance between the lower surface of the scrotum and the upper surface of the seat that arises due to differences amongst body shapes and clothing. For both of these reasons, this existing solution doesn't provide effective testes cooling for a variety of body shapes and clothing styles found in the general population. Furthermore, its flat elongated compliant shape provides unwanted cooling to other body parts such as the legs and prostate region; this unwanted cooling is possibly uncomfortable, and possibly reduces the duration of cooling of the scrotum and testes. Moreover, to maintain compliance, this solution uses a cold liquid that is kept above its freezing point, and this portion of volume can rely on heat capacity alone, and therefore can absorb much less heat by volume as compared to a frozen phase change material such as water or phase change gel occupying the same volume. Therefore, this existing solution can't provide as long a duration of cooling for a given volume as a device relying on the enthalpy of fusion for cooling.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a cooling pack that overcomes some of the drawbacks of known cooling packs, or at least provides a useful alternative thereto. Some aspects of this disclosure provide examples of such cooling packs.

For example, in some embodiments, a system and method is described which provides for effective and targeted cooling of the human crotch area while seated, namely to provide effective and targeted cooling of the scrotum and testes region of a human male. Some such embodiments may, alone or in combination in accordance with different embodiments, be easily adjustable for a variety of distances between scrotum and seat to accommodate a variety of body shapes and clothing, which may be comfortable, low-cost, and/or of limited complexity, which may be convenient to apply and remove without requiring privacy or garment adjustment, which may convenient to remove prior to activity or socially sensitive situations, and/or which may provide a long duration of cooling, to name a few exemplary features, advantages and/or objective of such embodiments. In accordance with one particular aspect, there is provided a cooling pack for cooling the crotch region of a human while seated on a seating surface, the cooling pack comprising: a tapered container for holding a cooling material therein, and defined by tapering upper and lower surfaces drawing into a tapered edge to be positioned between the crotch region and the seating surface in use, thereby providing cooling for the region.

In one embodiment, there is provided a cooling pack for cooling the crotch region of a human while seated on a seating surface, the cooling pack comprising: a tapered container for holding a cooling material therein, wherein the container is wedge-shaped having a tapering height defined by tapering substantially planar upper and lower surfaces drawing into a tapered edge, to be positioned and slidably adjusted fore or aft between the crotch region and the seating surface in use, thereby providing cooling for the crotch region.

In one embodiment, the container is made from plastic.

In one embodiment, the container further comprises a closure for emptying or filling the container with the cooling material.

In one embodiment, the cooling material is a phase-change material.

In one embodiment, the phase-change material is water.

In one embodiment, the container further comprises an insulating layer of insulating material.

In one embodiment, the insulating layer is defined on at least one of the upper and lower surfaces.

In one embodiment, the container further comprises distinct insulating layers for each of the upper and lower surfaces, wherein each of the distinct insulating layers defines a distinct thermal impedance value.

In one embodiment, the insulating layer is removable.

In one embodiment, the cooling pack further comprises a tapered form-fitting sleeve to receive the container therein.

In one embodiment, the form-fitting sleeve is manufactured of a thermally insulating material.

In one embodiment, the container is wedge-shaped.

In one embodiment, the tapering upper and lower surfaces are symmetric about the tapered edge.

In one embodiment, the container is symmetrically wedge-shaped.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein.

Figure 1:
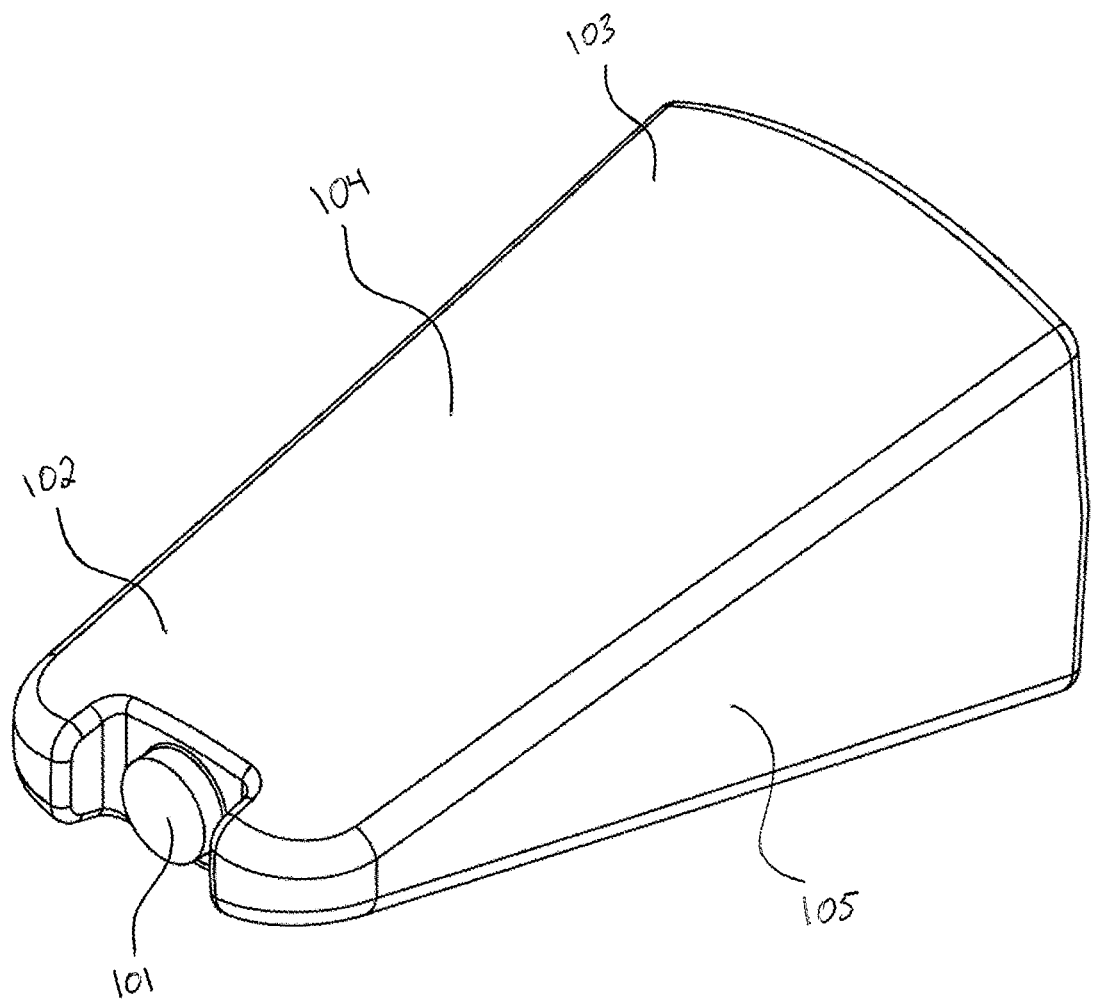
FIG. 1 is a perspective view of a tapered cooling pack defined by a tapered container that is substantially filled with water in a frozen format or other cooling material, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

The systems and methods described herein provide, in accordance with different embodiments, different examples of a tapered cooling pack for use, for example, in providing cooling for a crotch region of a human while seated. For example, in some applications, a tapered cooling pack as described herein may provide for the convenient and comfortable cooling of the scrotum and testes region of a human male while in a seated position. It will be appreciated that while examples are provided herein for use in the context of the human male anatomy, similar applications for the corresponding female anatomy may also be considered without departing from the general scope and nature of the present disclosure.

In some such embodiments, a tapered cooling or ice pack with insulation system and vapor barrier system is provided. The described embodiments, for example, may be consistently effective at cooling the scrotum and testes for most sitting postures and/or most seat conformities and/or most body geometries, may be easy to use and/or require no special clothing, may be comfortable, avoid getting the user wet, and/or rely on no expensive materials or processes to manufacture. These and other such features, benefits advantages and/or objectives, alone or in combination, will be readily appreciated by the skilled artisan upon reference to the following non-limiting description of specific embodiments.

In general, the tapered cooling pack will comprise a container with a tapered height shape which has an external height shorter at one end than at the opposing end, and wherein this container is substantially filled with a mass of phase change material that has a melting point below body temperature but above domestic freezer temperature, and wherein a phase change material (i.e. water) is intended to be used starting from a solid or frozen state and gradually melting when placed very near the scrotum and testes in order to absorb heat from the scrotum and testes thereby cooling them. While phase changing materials are considered specifically in these embodiments, other cooling materials such as gels or the like may equally be considered in a non-limiting fashion.

In this particular example, the tapered height shape of the plastic container forces the phase change material to freeze in a corresponding tapered height shape when placed into a domestic freezer, and thereafter when used to cool the scrotum and testes the combined tapered shape of the container and phase change material allows the user in a seated position to adjust the location of the container and its phase change material fore or aft to comfortably collapse the air gaps normally present between scrotum, clothing, and seat, thereby ensuring the right amount of contact between container, clothing, and scrotum to effectively transfer heat from the scrotum and testes to the phase change material without uncomfortably applying pressure to the scrotum and testes. While the most common and easily available phase change material is water, some embodiments may use water mixed with additives to improve its thermal properties or prevent bacterial growth. In other embodiments, other materials having similar or improved thermal/structural properties may be used instead.

In some embodiments, a fixed thermal impedance material is located within or adjacent to the upper surface of this tapered container, whereby this fixed thermal impedance material reduces the rate of heat flow from the scrotum and testes to the phase change material.

Other embodiments may also comprise two different fixed thermal impedance materials, one located within or adjacent to the top surface of the container, and one located adjacent to the bottom surface of the container, whereby the container may be used in either upright or upside-down orientation, and whereby the thermal impedance of the top layer may differ from or may be identical to the thermal impedance of the bottom layer, and whereby either thermal impedance reduces the rate of heat flow from the scrotum and testes to the phase change material.

In some embodiments, the container may also comprise an adjustable thermal impedance layer located within or adjacent to the upper surface, whereby the thermal impedance of this layer may be adjusted by adding, removing, re-orienting, or replacing the material present in order to adjust the rate of heat flow from the scrotum and testes to the phase change material.

In some embodiments, the container may also comprise a controlled thermal impedance material located within or adjacent to the other surfaces of the tapered container, whereby this controlled thermal impedance material reduces the rate of heat flow to the phase change material from other areas not intended to be cooled such as the seat surface, the inside of the thighs, and the air, in order to slow down the rate of unwanted phase change within the phase change material in order to prolong the duration of cooling of the scrotum and testes.

Figure 3:
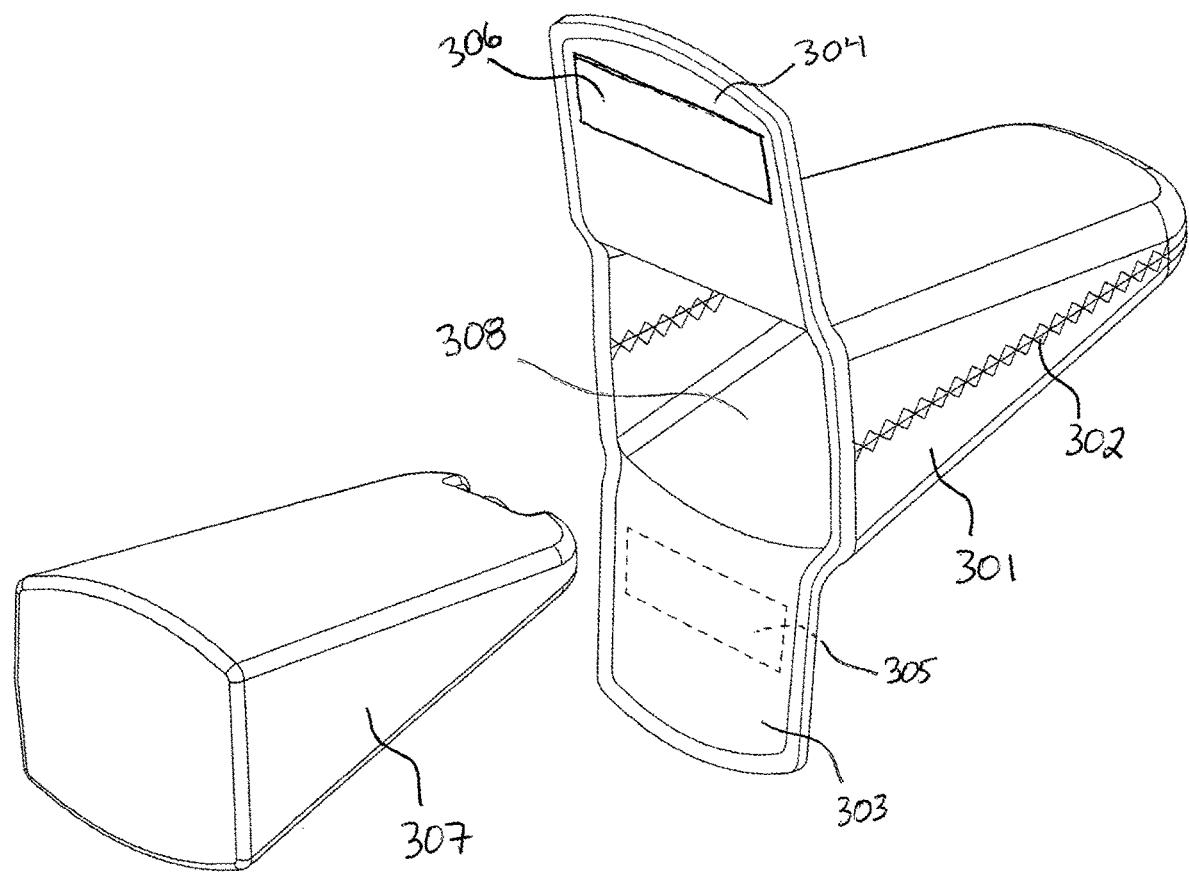
FIG. 3 is a perspective view of an open insulating sleeve receiving a tapered ice pack therein, in accordance with one embodiment.

With reference to FIG. 1, an exemplary embodiment of a tapered height plastic container 105 that is substantially filled with water (the phase change material) in a frozen format is shown. The tapered height upper surface 104 ("Contact Surface") has a shorter height region 102 and a taller height region 103, namely defining a wedge-shaped or tapered container in which an upper, substantially planar surface 104 and lower, substantially planar surface (not explicitly shown) draw into a tapered edge to be positioned between a crotch region and a seating surface in use, thereby providing cooling for the region. In the illustrated embodiment, the substantially planar upper and lower surfaces are slightly rounded in a lateral direction, as best seen in FIG. 3, and generally linearly tapering in a longitudinal direction. In this particular embodiment, fill nozzle 101 permits the container to be substantially filled with water at the factory, then sealed off with a welded or glued cap. Other embodiments may allow the container to be emptied and refilled by the user, for example, to reduce shipping costs, potential spills or leakage, or the like. Other prefilled or refillable cooling materials may also be considered, as will be readily appreciated by the skilled artisan. Other embodiments may have this fill nozzle located on another surface of the container i.e. on the taller end to permit a larger diameter cap.

In the illustrated embodiment, the upper surface 104 and lower surface illustratively tapper symmetrically toward the shorter height region 102, thereby defining a substantially symmetric wedged-shaped or tapered volume. While a substantially symmetric embodiment is illustrated herein as an exemplary implementation of the herein-described cooling pack, other tapering geometries may be considered herein without departing from the general scope and nature of the present disclosure, and apply to the embodiments illustrated by FIGS. 1 to 6 referenced herein.

The item embodied in FIG. 1 shall be hereafter referred to as "Tapered Ice Pack." It provides for effective and targeted cooling of the scrotum and testes, is easily adjustable for a variety of distances between scrotum and seat to accommodate a variety of body shapes and clothing, is comfortable, is low-cost, is not complex, is convenient to apply and remove without requiring privacy or garment adjustment, is convenient to remove prior to activity or socially sensitive situations, and provides a long duration of cooling.

Figure 2:
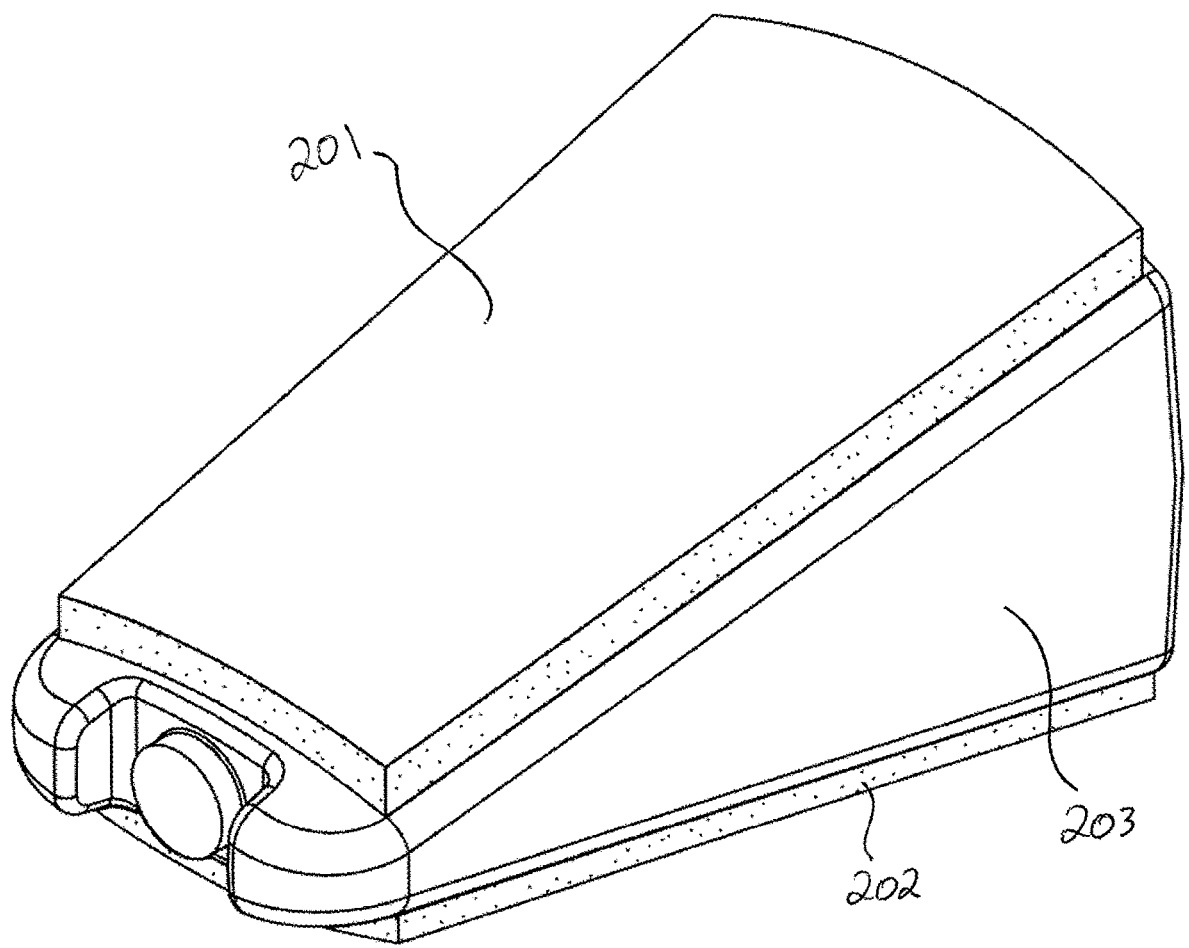
FIG. 2 is a perspective view of a tapered cooling pack with an insulating layer applied to a contact surface thereof, in accordance with another embodiment.

FIG. 2 shows an embodiment of a Tapered Ice Pack with an insulating layer 201 applied to the Contact Surface. This insulating layer reduces the rate of heat transfer from testes and scrotum to the Ice Pack to a controllable rate, in order to stabilize the testes temperature at a higher temperature than if insulation were not present. This is important to prevent discomfort due to excessively low scrotum and testes temperature, and for fertility applications to stabilize the scrotum and testes temperature at an optimal level slightly lower than body temperature where normal testicular function is optimized. Also shown is an example of insulation layers 202 applied to other surfaces that aren't the Contact Surface in order to reduce unwanted heat entering the ice pack that would accelerate its phase change and shorten its useful use period, and if placed on the sides of the Tapered Ice Pack 203, such insulation reduces unwanted heat flow away from parts of the body such as the inner thighs.

FIG. 3 shows an embodiment of an insulating sleeve 301 ("Sleeve") made of an insulating material cut to shape and stitch together 302 to permit near-complete envelopment of the Tapered Ice Pack 307. The Sleeve has an opening 308 permitting the Tapered Ice Pack to be inserted and removed. A first flap 303 and a second flap 304 are present to fold down and complete the envelopment once the Tapered Ice Pack is inserted. Once the flaps are folded down on top of each other in the right order, a first securing surface 305 and a second securing surface 306 come into contact with each other and mate to secure the flaps together and prevent the Tapered Ice Pack from sliding out of the Sleeve opening 308. Such mating may be a hook-and-loop type (e.g. Velcro) or a magnetic closure type or another closure mechanism.

Figure 4:
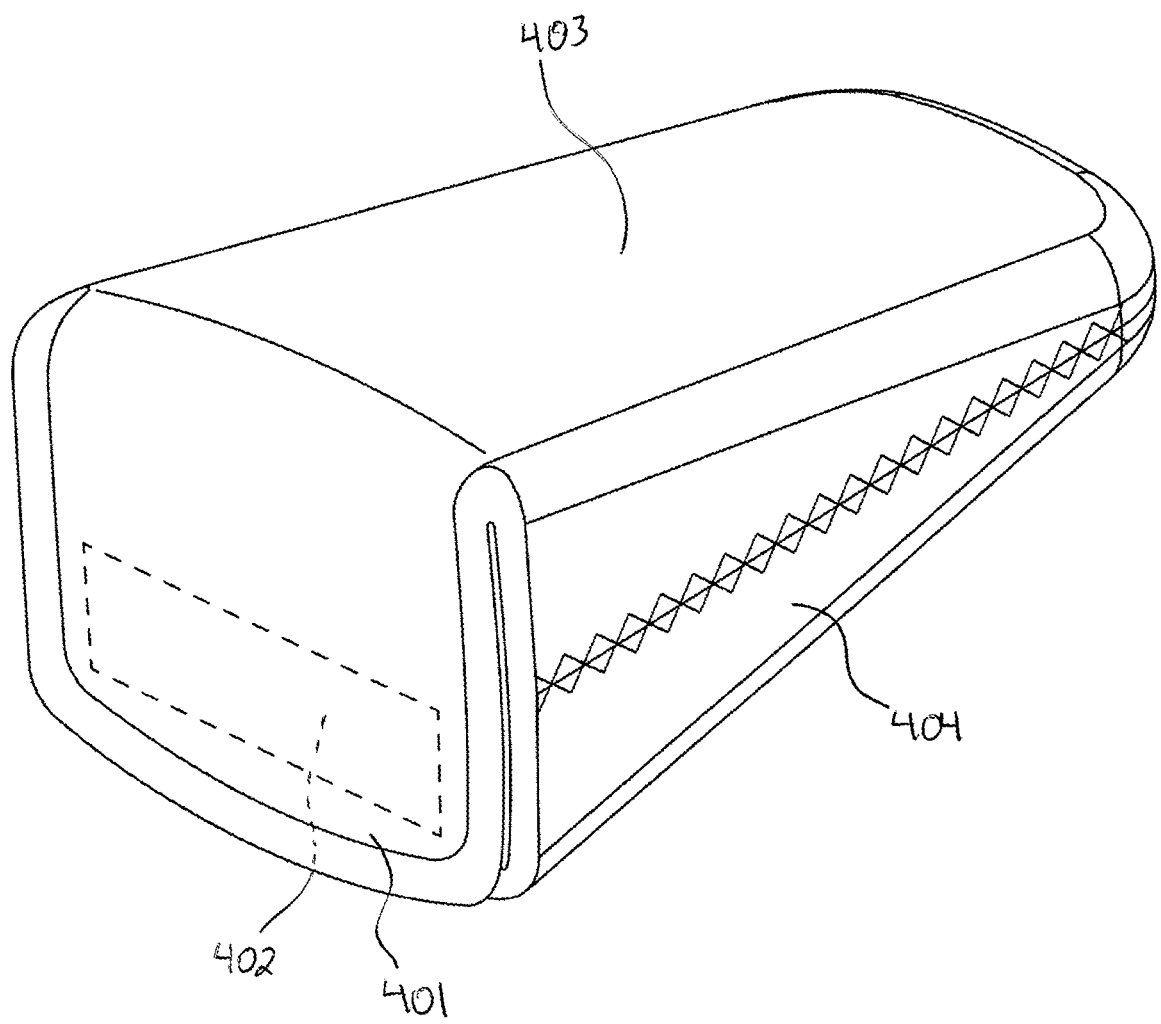
FIG. 4 is a perspective view of the insulating sleeve of FIG. 3 with the tapered ice pack contained therein.

FIG. 4 shows an embodiment of the "Enveloped Pack." Visible is the Sleeve with the outer flap 401 closed and mated at 402 to the inner flap (not visible). The Tapered Ice Pack is inside this sleeve and not visible. At the Contact Surface 403, the sleeve may be made of an insulating material such as Neoprene to reduce heat flow away from the scrotum and testes. At the sides 404, the sleeve may be made of an insulating material such as Neoprene to reduce heat flow away from the inner thighs. The sleeve on substantially all surfaces may be made of a vapor barrier material such as Neoprene in order to minimize contact of humid air against the cool surface of the Tapered Ice Pack that would otherwise cause condensation and unwanted pooling of water near the user's groin region. In addition to the Sleeve, one or more extra insulation layers may be added at the Contact Surface 403 to further reduce heat flow away from the Scrotum and Testes.

Figure 5:
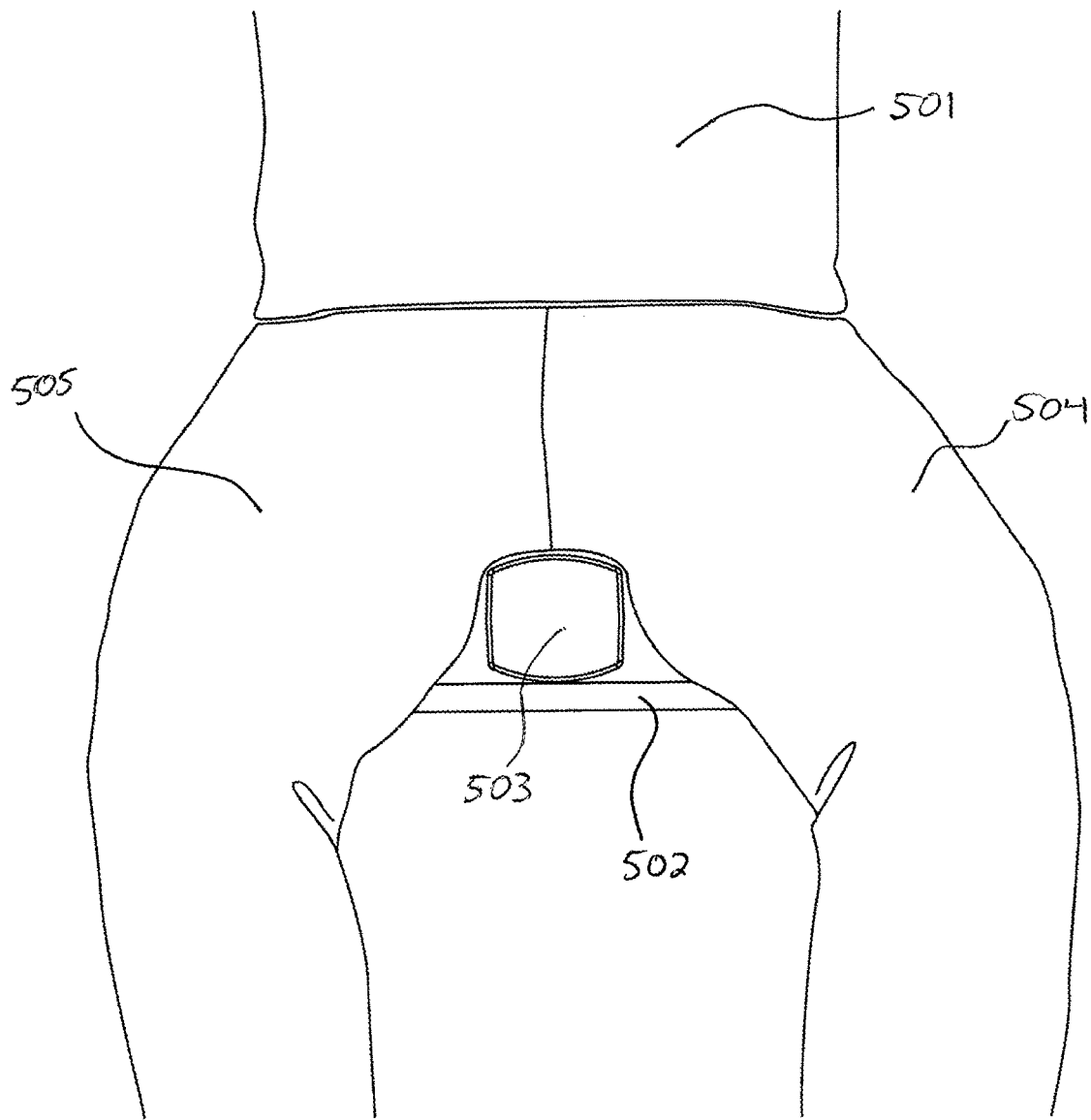
FIG. 5 is a front view of a human using a tapered cooling pack, in accordance with one embodiment.

FIG. 5 shows an exemplary embodiment as described herein in use. The Enveloped Pack 503 has been frozen in a domestic freezer immediately prior to use. The human user seen from the front has front torso 501 and legs 504 and 505, and sits on a seat 502. Once the user is seated, the Enveloped Pack is oriented in front of the user with shorter height region 102 toward the user and with Contact Surface facing generally upwards and slightly towards the user. The Enveloped Pack is slid rear-wards into a comfortable position between the user's legs, the seat upper surface, and the user's scrotum. The Enveloped Pack is slid rear-wards until the air gaps between the Contact Surface, the user's clothing, and the Scrotum have been minimized, stopping before the user experiences discomfort from too much upwards pressure on the scrotum and testes. The user maintains contact with the Contact Surface for a period of time.

Figure 6:
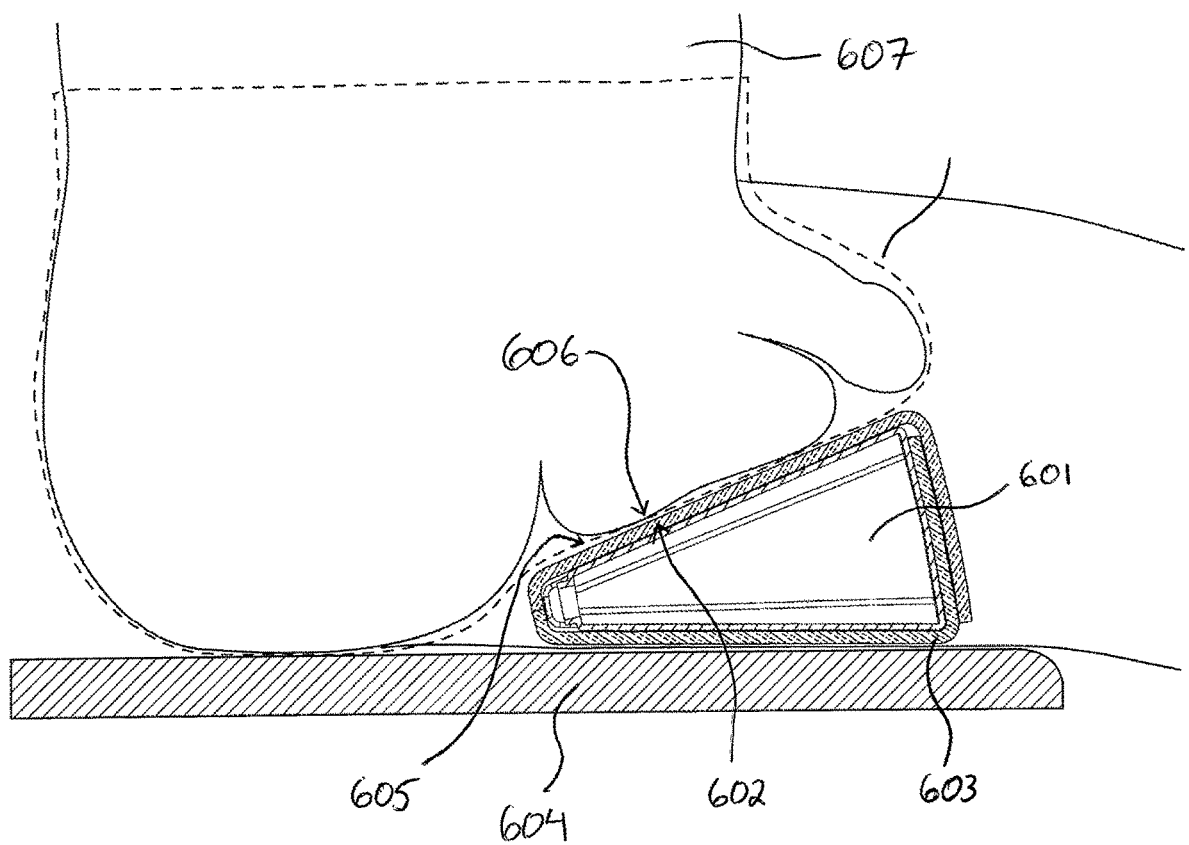
FIG. 6 is a cross-sectional view of a human male using a tapered cooling pack and enclosing sleeve, in accordance with one embodiment.

FIG. 6 shows a cross-sectional view of the embodiment of FIG. 5. The user front torso is at 607. The user is seated on seat 604. The user's scrotum lower surface 606 and clothing 605 are in substantial contact with the Enveloped Pack Contact Surface 602. The Sleeve 603 and Tapered Ice Pack 601 are seen in cross-section.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A cooling pack for cooling the crotch region of a human while seated on a seating surface, the cooling pack comprising:
   a tapered container for holding a cooling material therein, wherein said container is wedge-shaped having a tapering height defined by tapering substantially planar upper and lower surfaces drawing into a tapered edge, to be positioned and slidably adjusted fore or aft between the crotch region and the seating surface in use, thereby providing cooling for the crotch region.

2. The cooling pack of claim 1, wherein said container is made from plastic.

3. The cooling pack of claim 1, wherein said container further comprises a closure for emptying or filling the container with said cooling material.

4. The cooling pack of claim 1, wherein said cooling material is a phase-change material.

5. The cooling pack of claim 4, wherein said phase-change material is water.

6. The cooling pack of claim 1, wherein said container further comprises an insulating layer of insulating material.

7. The cooling pack of claim 6, wherein said insulating layer is defined on at least one of said upper and lower surfaces.

8. The cooling pack of claim 6, wherein said container further comprises distinct insulating layers for each of said upper and lower surfaces, wherein each of said distinct insulating layers defines a distinct thermal impedance value.

9. The cooling pack of claim 6, wherein said insulating layer is removable.

10. The cooling pack of claim 1, further comprising a tapered form-fitting sleeve to receive said container therein.

11. The cooling pack of claim 10, wherein said form-fitting sleeve is manufactured of a thermally insulating material.

12. The cooling pack of claim 1, wherein said tapering upper and lower surfaces are symmetric about said tapered edge.

13. The cooling pack of claim 1, wherein said container is symmetrically wedge-shaped.

* * * * *